(12) United States Patent
Karimpour

(10) Patent No.: US 11,064,680 B2
(45) Date of Patent: Jul. 20, 2021

(54) AUTOMATIC SYSTEM AND METHOD FOR INJECTING A SUBSTANCE INTO AN ANIMAL

(71) Applicant: Applied LifeSciences and Systems, LLC, Raleigh, NC (US)

(72) Inventor: Ramin Karimpour, Raleigh, NC (US)

(73) Assignee: Applied LifeSciences and Systems LLC, Raleigh, NC (US)

(*) Notice: Subject to any disclaimer, the term of this patent is extended or adjusted under 35 U.S.C. 154(b) by 397 days.

(21) Appl. No.: 15/775,733

(22) PCT Filed: Nov. 11, 2016

(86) PCT No.: PCT/US2016/061565
§ 371 (c)(1),
(2) Date: May 11, 2018

(87) PCT Pub. No.: WO2017/083674
PCT Pub. Date: May 18, 2017

(65) Prior Publication Data
US 2018/0368364 A1    Dec. 27, 2018

Related U.S. Application Data

(60) Provisional application No. 62/349,981, filed on Jun. 14, 2016, provisional application No. 62/254,737, filed on Nov. 13, 2015.

(51) Int. Cl.
*A01K 13/00* (2006.01)
*A01K 61/13* (2017.01)
(Continued)

(52) U.S. Cl.
CPC .......... *A01K 13/003* (2013.01); *A01K 45/00* (2013.01); *A01K 61/13* (2017.01); *A61B 5/0033* (2013.01);
(Continued)

(58) Field of Classification Search
CPC ........ A01K 13/003; A01K 61/13; A61D 7/00; A61M 5/14244; A61M 2005/14252;
(Continued)

(56) References Cited

U.S. PATENT DOCUMENTS 3,255,731 A * 6/1966 Girard .................... A01K 63/04
119/224
3,774,578 A * 11/1973 Randolph .............. A61D 19/02
119/714
(Continued)

FOREIGN PATENT DOCUMENTS

FR        2885030 A    11/2006
JP        1998192310    7/1998
(Continued)

OTHER PUBLICATIONS

Office Action issued by Federal Service for Intellectual Property (Russia) against Application No. 2018117356/10 (027024) dated Mar. 4, 2020.
(Continued)

*Primary Examiner* — Tien Q Dinh
*Assistant Examiner* — Katelyn T Truong
(74) *Attorney, Agent, or Firm* — Kathleen Lynch; Law Office of Kathleen Lynch PLLC

(57) ABSTRACT

A system and method for automatically delivering a substance to an animal or fish including a positioning system that positions each animal singularly and a sensor that detects the location of a predetermined targeted area on the animal. The system further includes a delivery device for delivering a substance to the targeted area. The position of the delivery device may be adjustable. The delivery device is in communication with the sensor. The delivery device adjusts its position in response to the data received from the sensor and delivers a substance to the targeted area.

18 Claims, 13 Drawing Sheets

(51) Int. Cl.
| | |
|---|---|
| *G16H 20/17* | (2018.01) |
| *A01K 45/00* | (2006.01) |
| *A61B 5/00* | (2006.01) |
| *A61D 7/00* | (2006.01) |
| *G16H 50/20* | (2018.01) |
| *A61D 17/00* | (2006.01) |
| *A61D 19/00* | (2006.01) |
| *A61D 1/02* | (2006.01) |
| *B65G 15/30* | (2006.01) |
| *A61D 3/00* | (2006.01) |
| *G06T 7/00* | (2017.01) |
| *A61M 5/30* | (2006.01) |
| *A61M 5/42* | (2006.01) |

(52) U.S. Cl.
CPC .............. *A61B 5/0077* (2013.01); *A61B 5/43* (2013.01); *A61B 5/70* (2013.01); *A61B 5/7282* (2013.01); *A61D 1/025* (2013.01); *A61D 3/00* (2013.01); *A61D 7/00* (2013.01); *A61D 17/00* (2013.01); *A61D 19/00* (2013.01); *A61M 5/30* (2013.01); *A61M 5/427* (2013.01); *B65G 15/30* (2013.01); *G06T 7/001* (2013.01); *G16H 20/17* (2018.01); *G16H 50/20* (2018.01); *A61B 2503/40* (2013.01); *A61B 2576/00* (2013.01); *A61M 2250/00* (2013.01); *B65G 2201/02* (2013.01); *G06T 2207/30128* (2013.01); *Y02A 90/10* (2018.01)

(58) Field of Classification Search
CPC ...... A61M 5/14248; A61M 2005/3022; A61M 5/42; A61M 5/425; A61M 5/427; A61M 2210/083; A61M 25/02; A61M 2025/0206; A61M 2025/0253; A61M 2025/026; A61M 2025/0213
See application file for complete search history.

(56) References Cited

U.S. PATENT DOCUMENTS

| | | | | |
|---|---|---|---|---|
| 4,449,968 | A | | 5/1984 | Peterson |
| 4,709,660 | A | * | 12/1987 | Hrushesky .............. A61D 3/00 |
| | | | | 119/751 |
| 4,850,997 | A | | 7/1989 | DuBose |
| 5,780,448 | A | | 7/1998 | Davis |
| 6,396,938 | B1 | | 5/2002 | Tao et al. |
| 7,018,638 | B2 | | 3/2006 | Chu et al. |
| 8,397,670 | B2 | | 3/2013 | Van Den Berg |
| 9,050,281 | B2 | | 6/2015 | Lang et al. |
| 2001/0035370 | A1 | | 11/2001 | Yavnai et al. |
| 2002/0112724 | A1 | | 8/2002 | Newhouse et al. |
| 2007/0055200 | A1 | | 3/2007 | Gilbert |
| 2008/0196728 | A1 | | 8/2008 | Ho |
| 2009/0000915 | A1 | | 1/2009 | Nadreau et al. |
| 2010/0310589 | A1 | | 12/2010 | Kumar |
| 2012/0247395 | A1 | * | 10/2012 | Koba .................... A01K 63/00 |
| | | | | 119/207 |
| 2014/0174371 | A1 | * | 6/2014 | Ulriksen ................ A01K 63/00 |
| | | | | 119/219 |
| 2015/0125509 | A1 | * | 5/2015 | Blaser .................... A01N 47/34 |
| | | | | 424/442 |
| 2015/0320010 | A1 | | 11/2015 | Schippers |
| 2017/0128182 | A1 | * | 5/2017 | Yamada .................. A61M 5/30 |
| 2017/0172114 | A1 | * | 6/2017 | Halse ...................... B05B 1/02 |
| 2018/0317457 | A1 | * | 11/2018 | Bastos .................... A61D 7/00 |

FOREIGN PATENT DOCUMENTS

| | | |
|---|---|---|
| KR | 101071880 B | 10/2011 |
| WO | 2012008843 A1 | 1/2012 |
| WO | WO/2012/008843 | 1/2012 |
| WO | WO/2012/017359 | 2/2012 |
| WO | 2015112786 A1 | 7/2015 |

OTHER PUBLICATIONS

English translation of Office Action issued by Federal Service for Intellectual Property (Russia) against Application No. 2018117356/10(027024) dated Mar. 4, 2020.

Substantive Examination Report issued by Directorate General of Intellectual Property (Indonesia) against Application No. PID201804018 dated May 27, 2020.

English summary, dated Jun. 3, 2020, of Substantive Examination Report issued by Directorate General of Intellectual Property (Indonesia) against Application No. PID201804018 dated May 27, 2020.

Communication pursuant to Article 94(3) EPC from the European Patent Office against Application No. 16865084.4-1011 dated Mar. 12, 2020.

Office Action issued by National Institute of Industrial Property (Brazil) against Application No. BR112018009633-4 dated Jun. 9, 2020 (5 pages).

English translation of Office Action issued by Federal Service for Intellectual Property Brazil) against Application No. BR112018009633-4 dated Jun. 9, 2020 (2 pages).

Second Office Action issued by National Intellectual Property Administration (China) against Application No. 201680065820.6 dated Jul. 21, 2020 (10 pages).

English translation of Second Office Action issued by National Intellectual Property Administration (China) against Application No. 201680065820.6 dated Jul. 21, 2020 (11 pages).

Office Action issued by United States Patent and Trademark Office against U.S. Appl. No. 15/775,608 dated Jul. 17, 2020 (10 pages).

Second Office Action issued by National Intellectual Property Administration (China) against Application No. 201680065988.7 dated Jul. 31, 2020 (8 pages).

English translation of Second Office Action issued by National Intellectual Property Administration (China) against 201680065988.7 dated Jul. 31, 2020 (3 pages).

First Office Action issued by National Intellectual Property Administration (China) against Application No. 201680065986.8 dated Jul. 22, 2020 (9 pages).

English translation of First Office Action issued by National Intellectual Property Administration (China) against Application No. 201680065986.8 dated Jul. 22, 2020 (13 pages).

* cited by examiner

AUTOMATIC SYSTEM AND METHOD FOR INJECTING A SUBSTANCE INTO AN ANIMAL

PRIORITY

This application claims priority from U.S. provisional patent application Ser. No. 62/254,737, filed Nov. 13, 2015, and U.S. provisional patent application Ser. No. 62/349,981 filed Jun. 14, 2016. The contents of each are incorporated herein in their entirety.

BACKGROUND

Bacterial, viral and fungal infections and other diseases are often prevented or treated through vaccination, or delivery of a drug to a subject. In all animals, and in particular, vertebrates or fish, and invertebrates, such as crustaceans, the delivery of vaccines, biologics and other medicine is often delivered to prevent disease, death or to maintain overall good health. In many livestock and fish farming operations, it is a challenge to ensure that all animals have been effectively treated. The number and variation in the size of the subject makes vaccination and delivery of other medicine to each subject a challenge.

Turning now to the poultry industry in particular, there are several current methods in which fertilized eggs or chickens are treated with medicine. These include:
1) Automated Vaccination in the hatchery performed "in ovo" (within the egg) on day 18 or 19;
2) Automated Mass Spray Vaccination in the hatchery performed "post-hatch";
3) Manual Injection Vaccination in the hatchery performed "post-hatch";
4) Vaccination/Medication added to the feed or water in the "Growth Farm"; and
5) Vaccination/Medication sprayed on the chicks either manually or by mass-sprayers.

While the poultry industry spends over $3 billion on vaccines and other pharmaceuticals on annual basis, the return on their investment is not guaranteed due to the challenges with the manner in which the vaccines or other substances are delivered. Each aforementioned method has shown noticeable and significant inadequacies. First, the automated vaccination in the hatchery performed in ovo on E18/19 is highly popular. However, there are drawbacks with this system. First, many vaccines of interest are either not available for in ovo application and may not become available by the nature of the disease and/or the conjugates necessary to carry the active molecules/particles cannot be applied in ovo. In addition, current practice of in ovo vaccination requires the punching/piercing of a whole in the egg on day 18 or 19. The delivery requires holding the egg in place by some mechanical means while extending a needle into the egg and administering the injection of the vaccine/drug. This practice may allow pathogens and bacteria to enter the egg and negatively impact the embryo. During the in ovo vaccination, undesirable eggs (rotten or eggs containing dead embryos) are also in contact with the mechanical means of holding eggs in a stationary position before getting punched/pierced and the needles. Thus there is a high probability of spreading undesirable contamination into other eggs and the vaccination system. Thus, allowing transfer of contamination to subsequent live eggs during further processing.

To reduce the impact of this contamination transfer, the industry started to introduce and inject antibiotics into eggs as a part of in ovo vaccination. However, consumers are moving away from poultry treated with antibiotics. As such the industry is feeling the need to find alternative methods to treat the same diseases in a different manner that will maintain flock health while eliminating the use of antibiotics.

While "post-hatch" manual vaccination in the hatchery may be considered more reliable than other methods, studies have shown that this practice also is lacking in reliability, repeatability and causes chick injuries and death. Hatcheries face challenges in finding reliable vaccinators and the increasing daily production rates makes this more challenging. This heightens the challenge to ensure all chicks are effectively vaccinated which adds to the overall cost. In addition, because the chicks must be handled during vaccination, there is a risk of injury or death to the chick in the event the chick is harmed during handling. Moreover, because the workers must vaccinate multitudes of chicks, the workers are subject to repetitive stress injuries. This results in an economic and productivity loss to the poultry producers.

An alternative approach has been to add the vaccination/medication to the feed or water in the farm. This methodology has proven to be only partially effective, due to the fact that for the most part bacteria, pathogens and parasites in the chick's digestive system have become resistant to the drugs. Other factors that contribute to partial efficacy of this method include the lack of uniformity in the drinking lines, uneven doses delivered as a result of uneven amounts eaten or drunk, and that some vaccines have a very short half-life in water or feed.

With regard to the fish farming industry, fish have become an increasingly greater source of food for human consumption. The state of the oceans, rivers and lakes are such that fish farming provides a more reliable source for consumable fish. However, fish farms or hatcheries have similar challenges to the poultry industry in keeping all of the fish healthy.

Fish hatcheries raise the fish from eggs and place similarly aged fish in the same tanks. Large quantities of fish are placed in large tanks and provided with food to grow. The large quantities of fish in tight quarters within a tank can result in the spreading of a disease quickly and with significant economic consequences.

Often any vaccine, drugs and anti-parasitics may be delivered via application of solutions in the fish tanks or the fish feed. However, some conditions or diseases may not be treatable through aforementioned methods. In such cases, fish need to be injected with vaccines and other biologicals on individual basis. Current fish injection methods require removal of the feed from the fish for a period of time before sedation of the fish prior to said operation. The sedated and hungry fish are then moved via mechanical means and either manually or automatically are injected via manual or mechanical positioning means. These operations have shown to be harsh on the fish and resulting in increased mortality and extensive costs.

In a similar manner, in many livestock farm operations, it is a laborious challenge to ensure that all animals have been effectively treated. The number and variation in the size of the subject makes vaccination and delivery of other medicine to each subject a challenge.

Turing now to swine, similar challenges exist with regard to the ability to vaccinate or otherwise treat all piglets in any particular farm. It is important to ensure that each piglet is effectively treated, otherwise one sick piglet could infect an entire farm with devastating economic consequences.

With regard to swine, there are some vaccines or treatments that are preferably delivered via the nasal cavity. However, the ability to deliver the effectively can be challenging in that young piglets are not easily kept still long enough to delivery an effective dosage and movement during delivery may harm the piglet's nasal cartilage or brain.

Regardless of where/how vaccines and medications are administered, current methods have proved to be not adequately effective for some important applications. Failure to effectively deliver treatment or vaccinate all animals or fish within a larger population can lead to disease outbreaks and significant economic losses. These inadequacies combined with new market trend to eliminate the application of antibiotics in the farming of animals and fish, including the medicated feed additives ("MFAs"), are the main drivers for the embodiments described herein. The challenge in mass delivery is ensuring that each animal has received the effective dose.

SUMMARY

The embodiments described herein are directed to a system for automatically delivering a substance to a predetermined area of an animal. The system includes a sensing device for detecting the relative position of a predetermined delivery area on an animal, and a positioning device that positions an animal individually. The system further includes an image capture device to capture at least one image of the relative position of the predetermined delivery area on the animal and a delivery system to deliver a predetermined dosage of a substance to the predetermined delivery area of the animal. The system also includes system controller in communication with the sensing device, positioning device, image capture device and delivery system. When the sensing device senses the location/position of the animal and shares the information with the system controller, the system controller processes the image, determines the location of the predetermined area and positionally adjusts the delivery system to deliver the substance to the predetermined delivery area on the animal.

DESCRIPTION OF THE DRAWINGS

Figure 1:
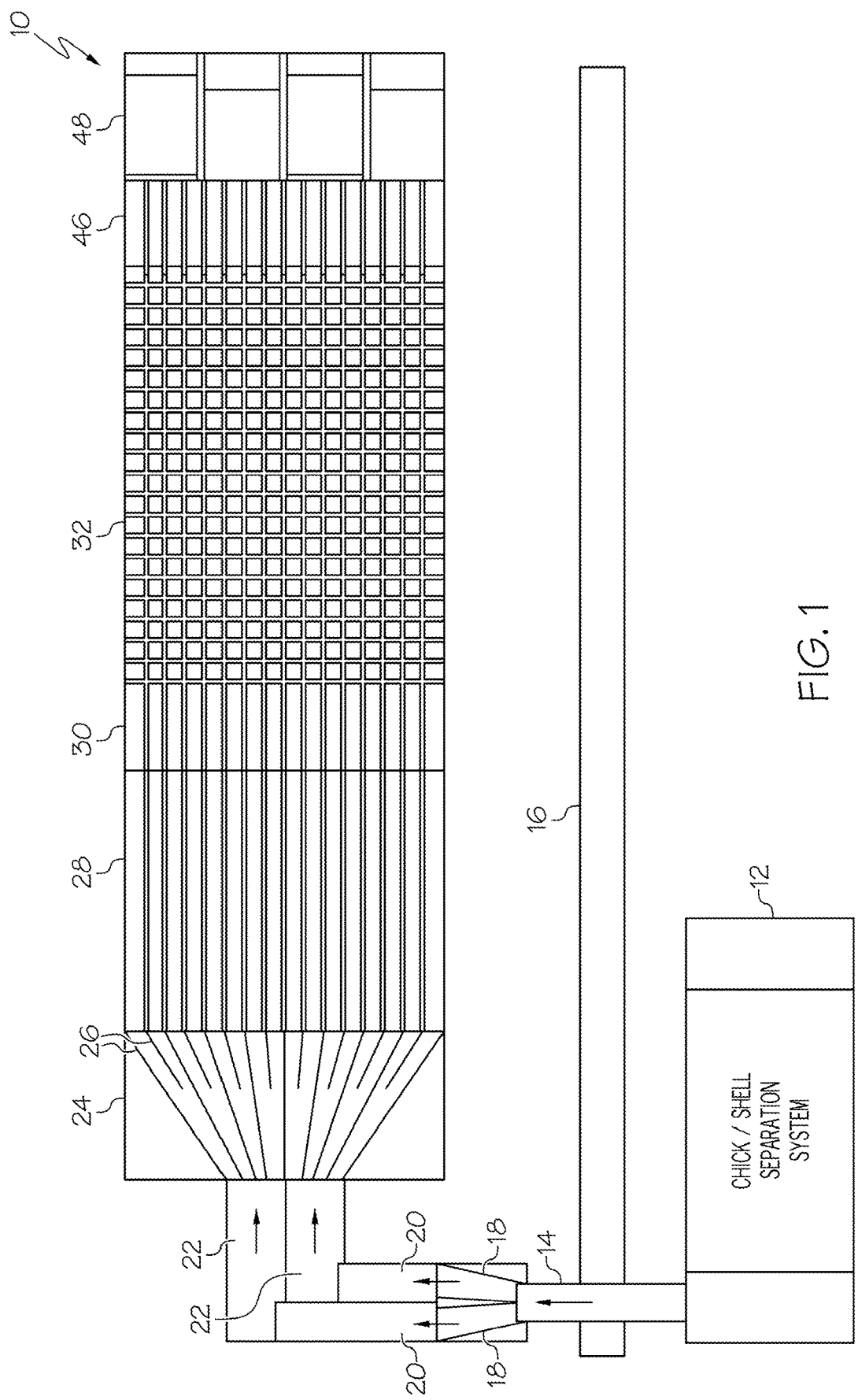
Figure 2:
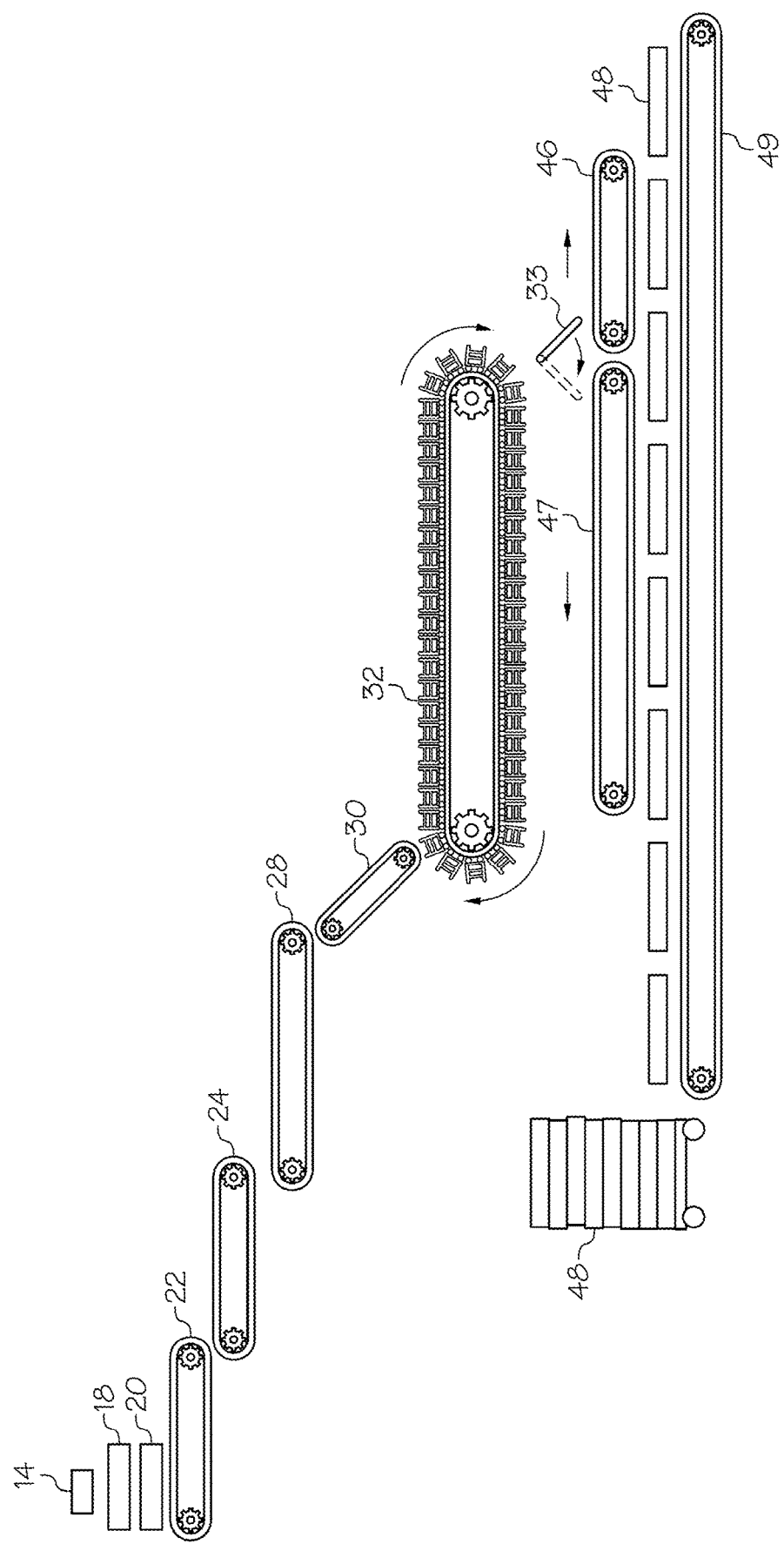
Figure 3:
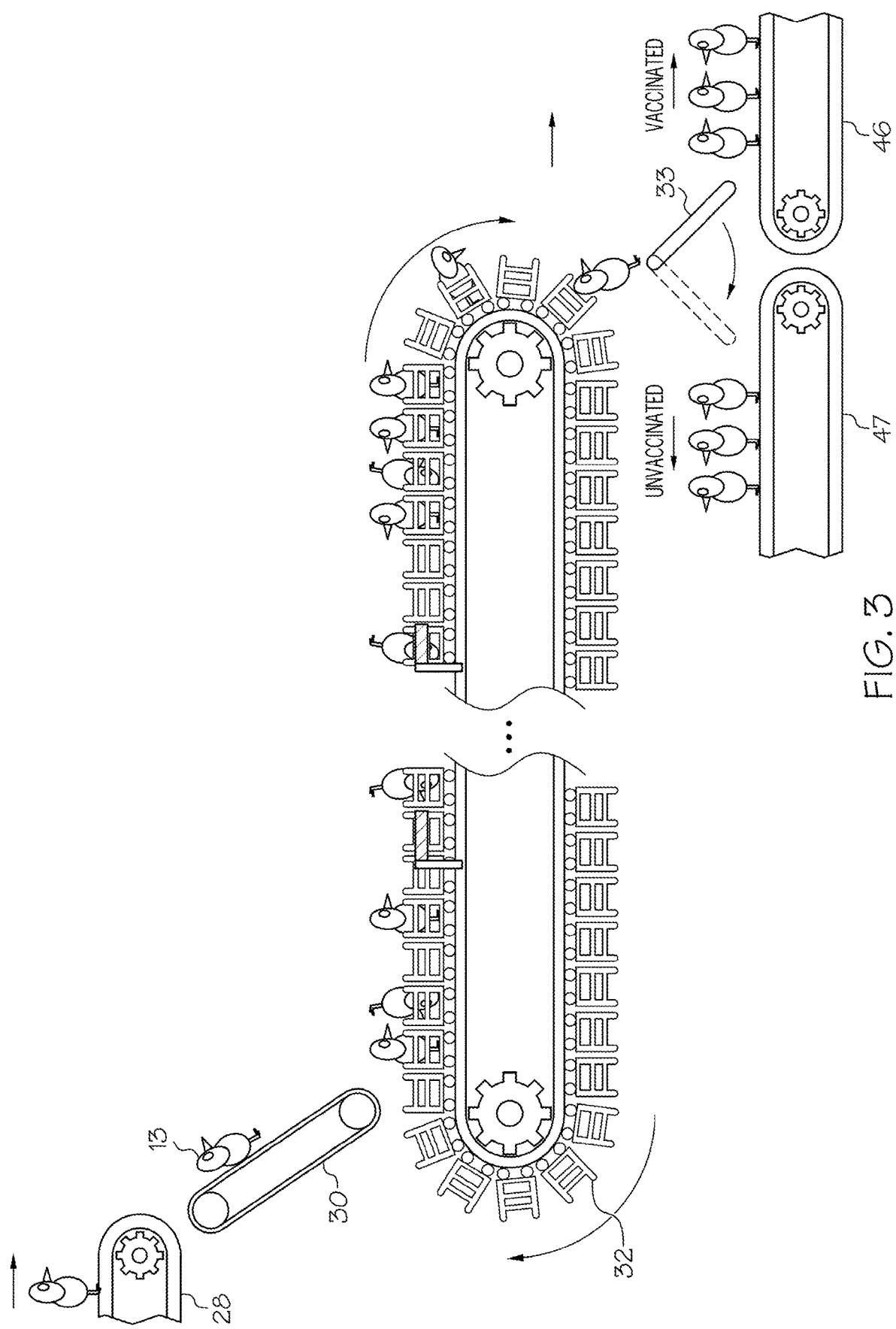
Figure 4:
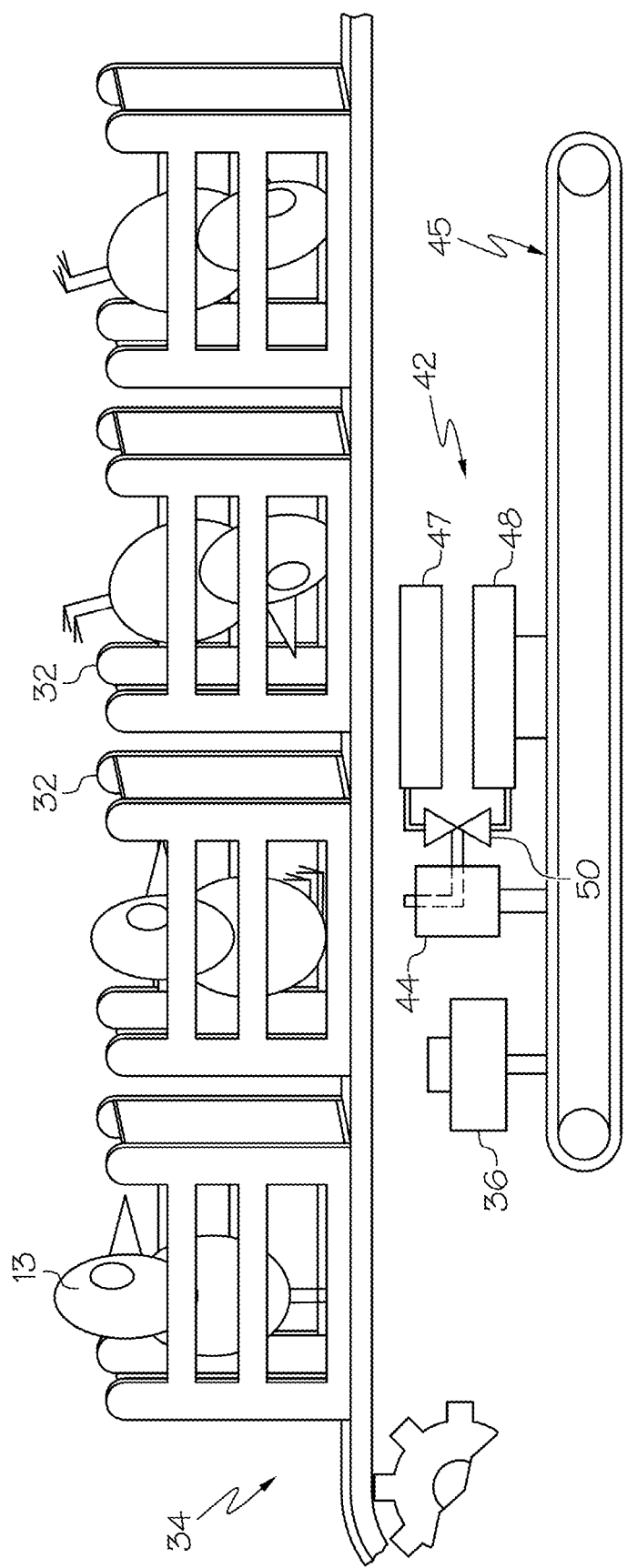
Figure 5:
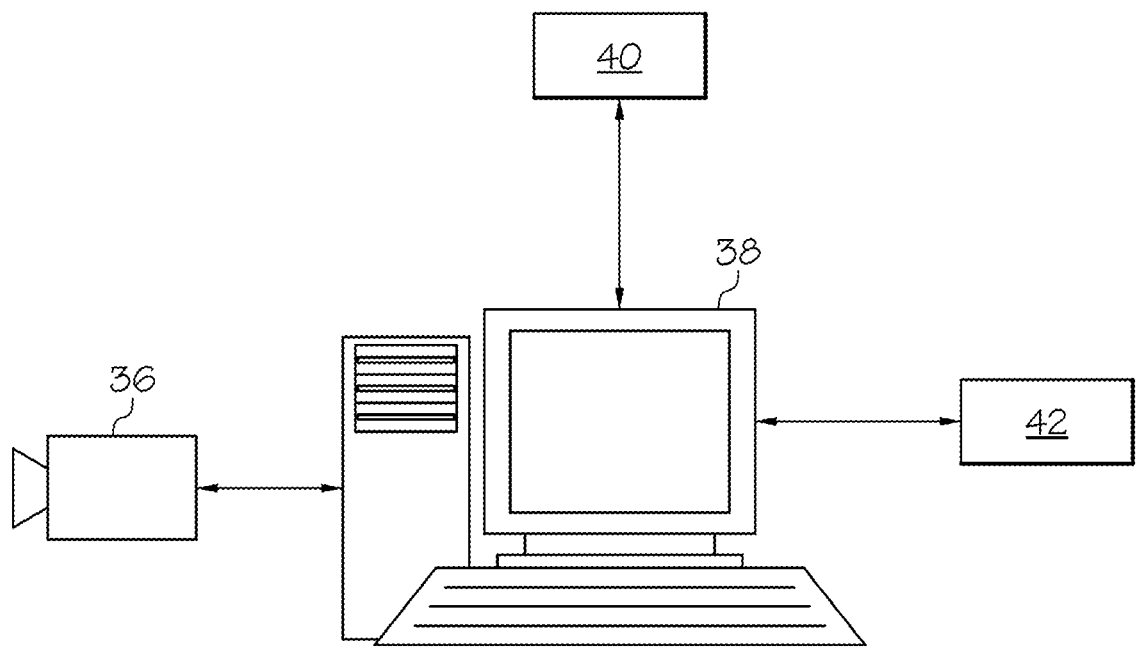
Figure 6:
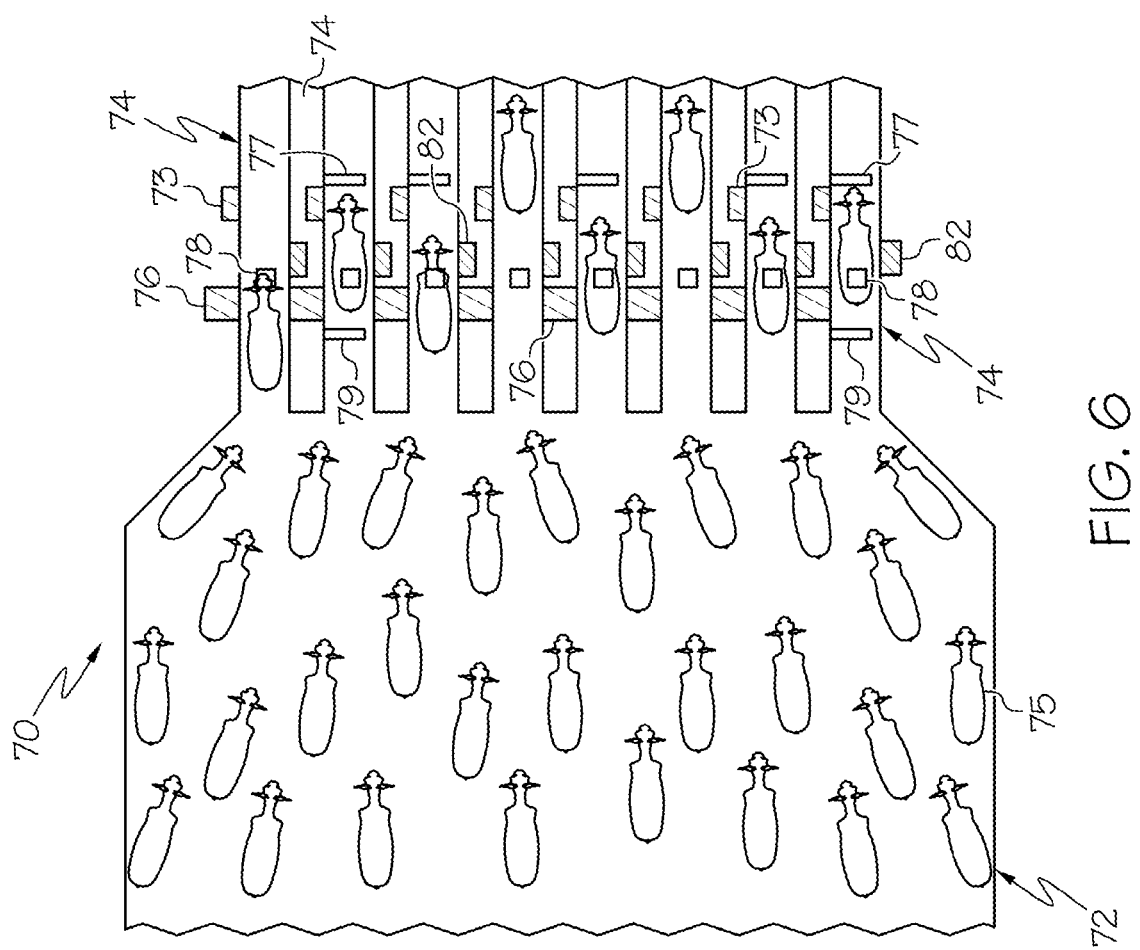
Figure 7:
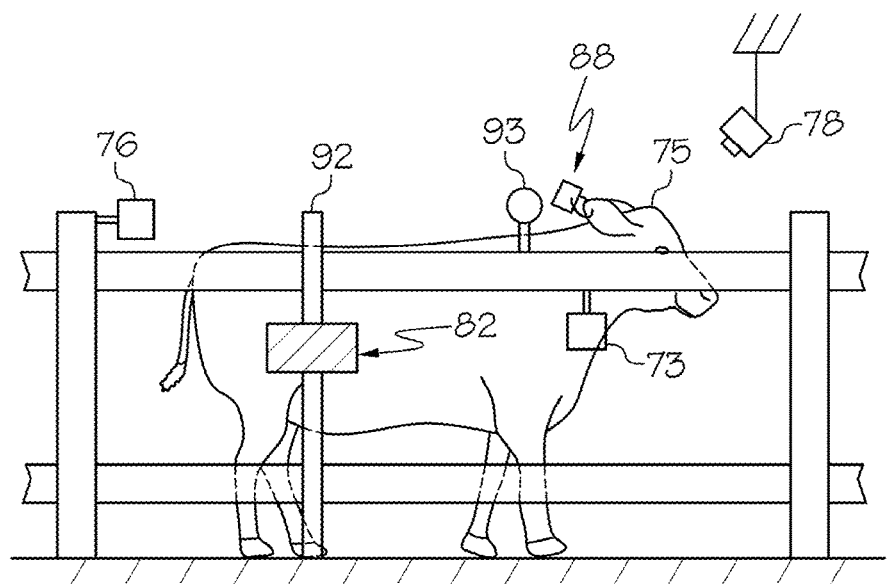
Figure 8:
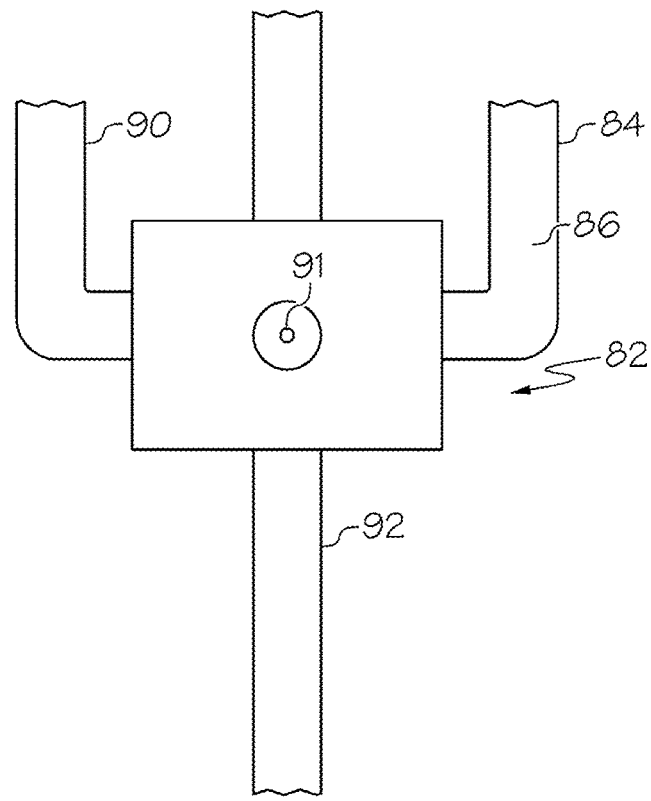
Figure 9:
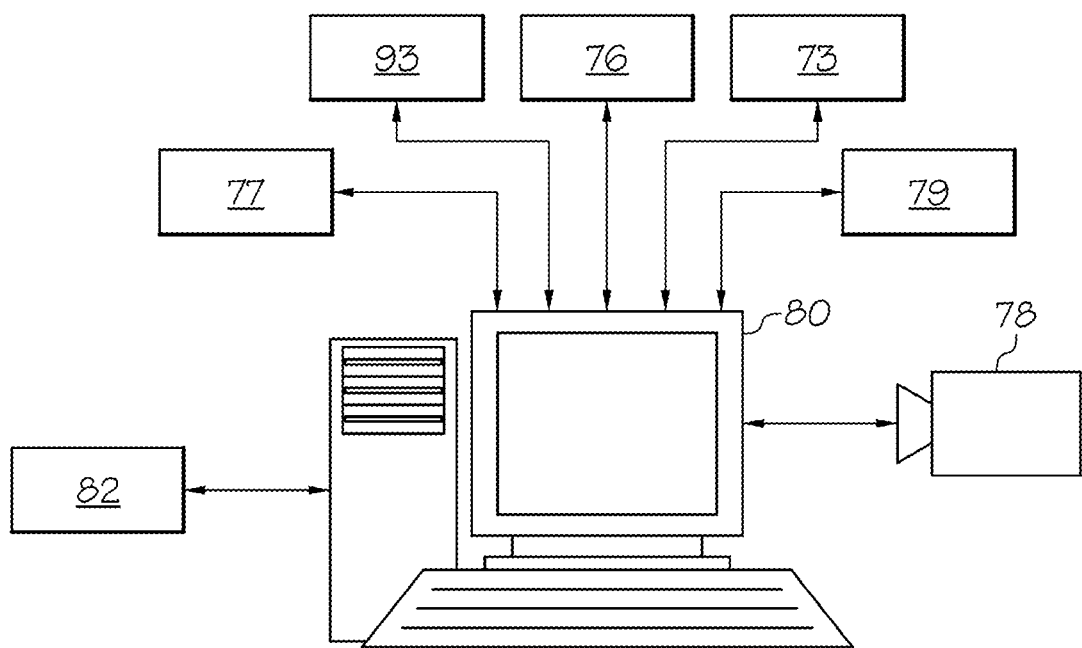
Figure 10:
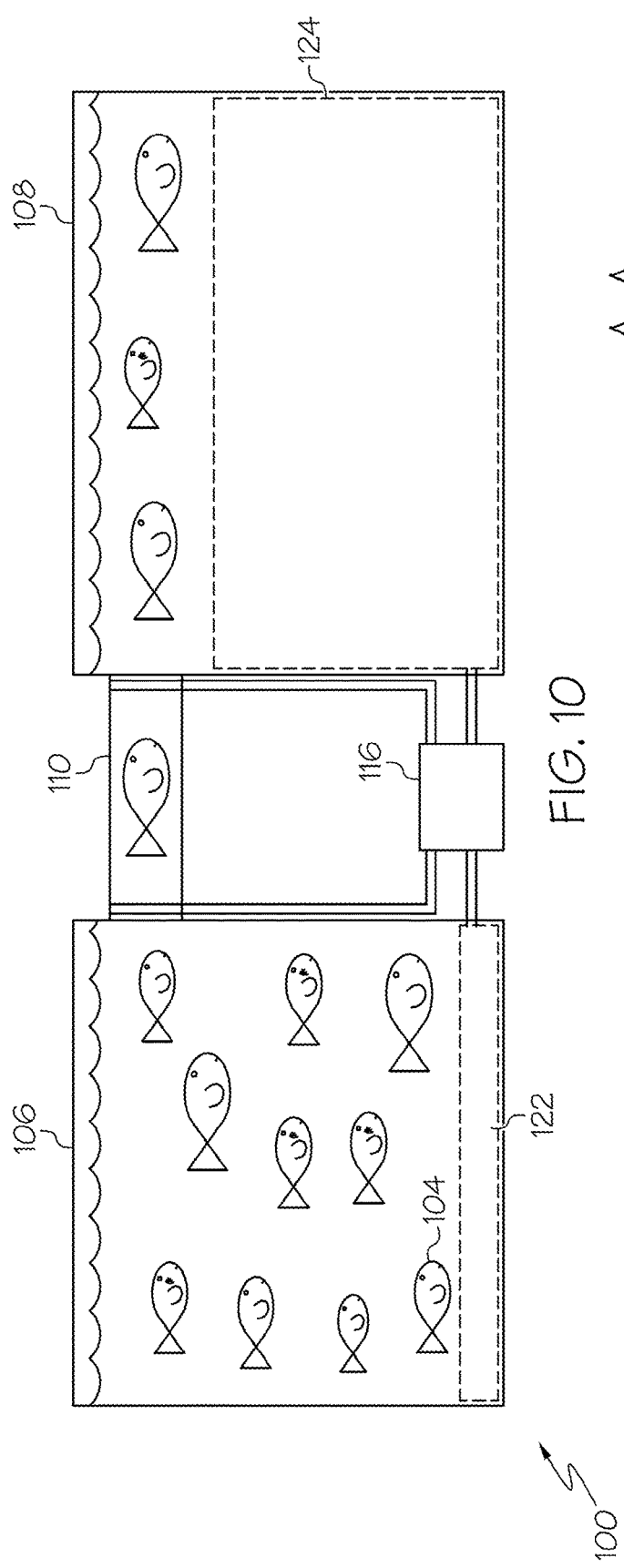
Figure 12:
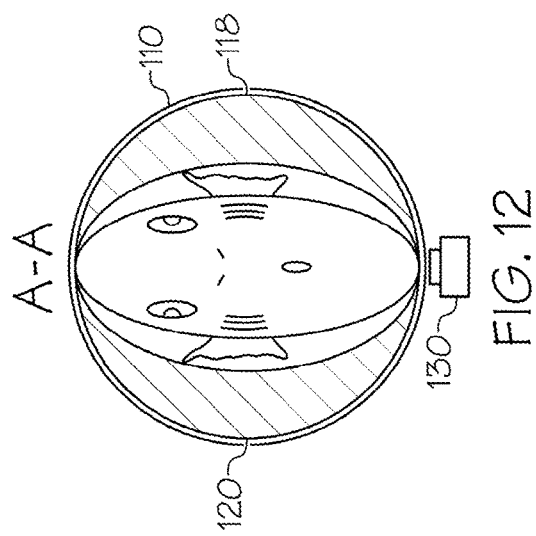
Figure 11:
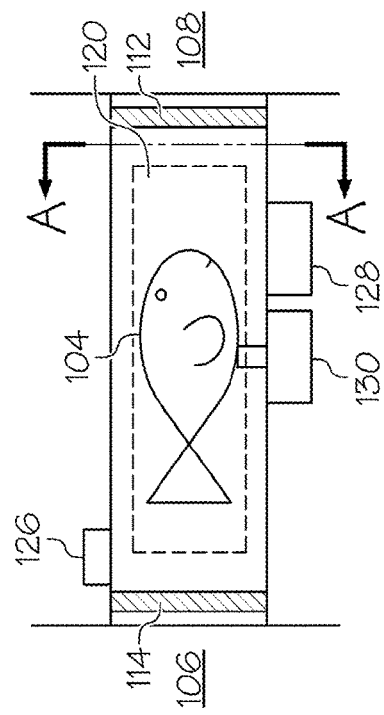
Figure 13:
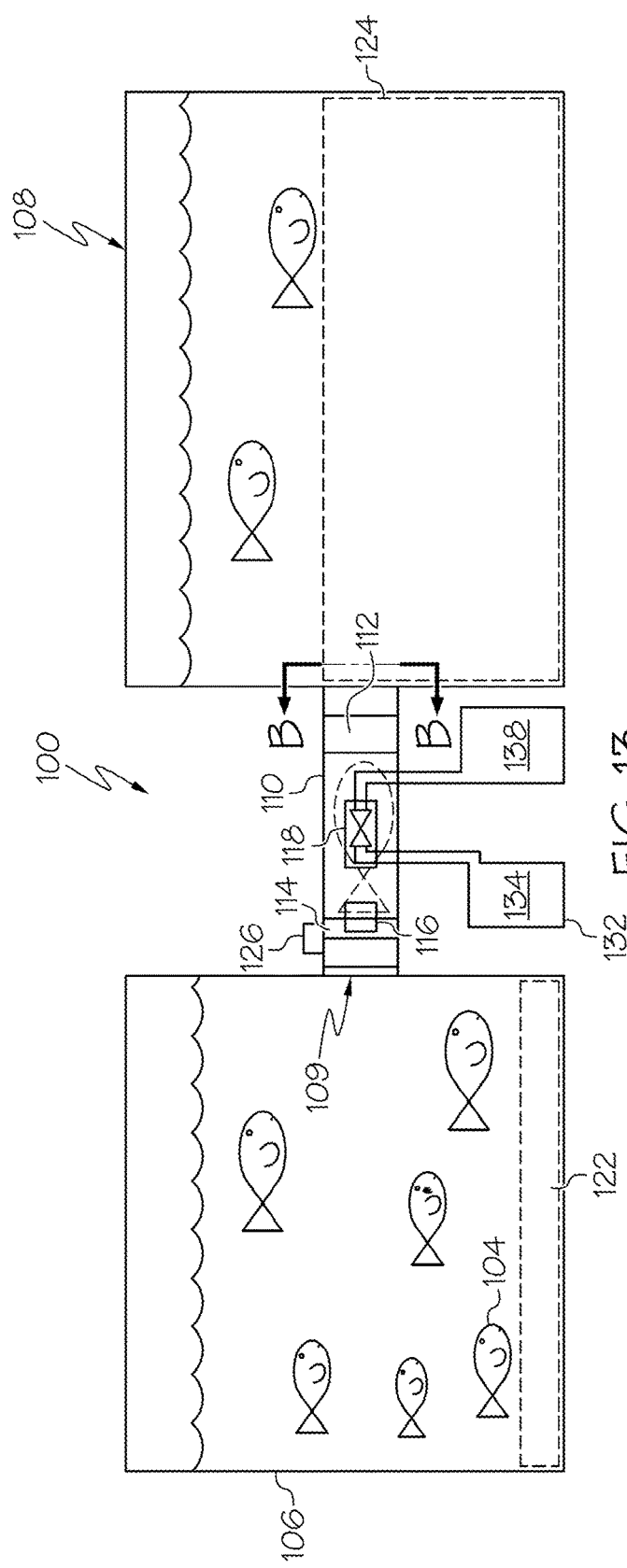
Figure 14:
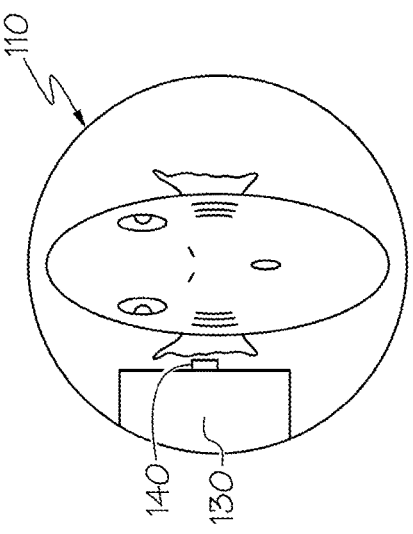
Figure 15:
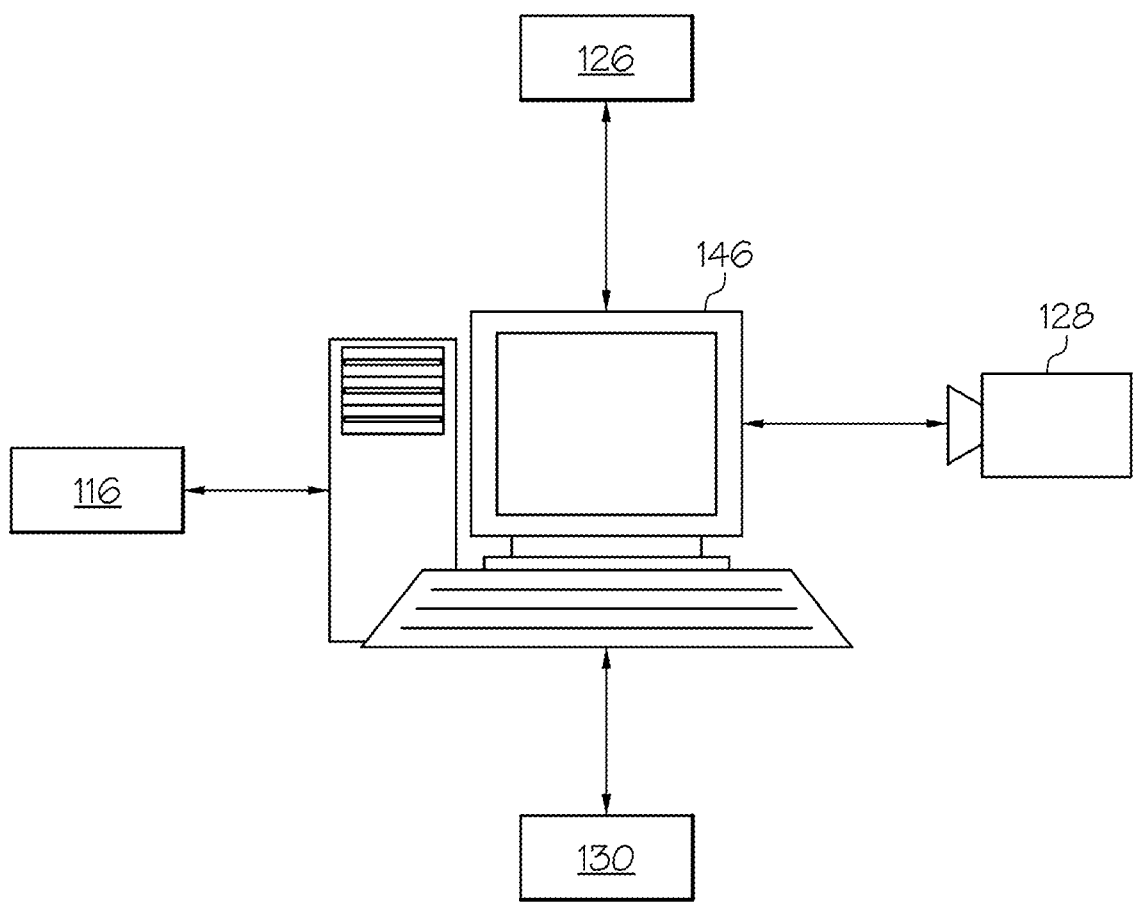
Figure 16:
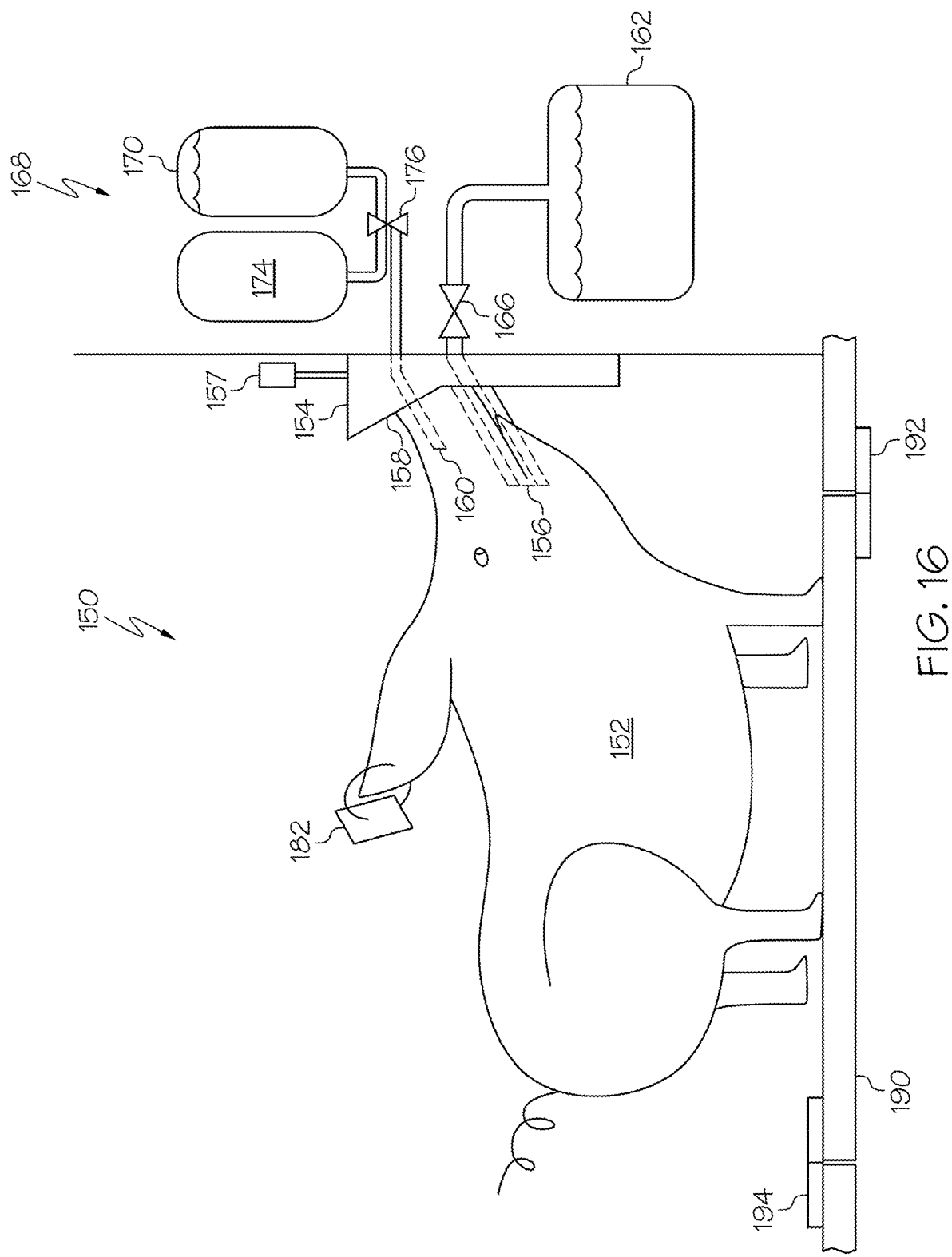

Having thus described various embodiments of the present disclosure in general terms, reference will now be made to the accompanying drawings, which are not drawn to scale and do not include all components of the system, and wherein:

FIG. 1 is a schematic top view of the first embodiment;

FIG. 2 is a schematic side view of the embodiment of FIG. 1;

FIG. 3 is a partial enlarged side view of a portion of the embodiment of FIG. 1 in use;

FIG. 4 is a partial enlarged perspective view of the embodiment of FIG. 1 in use;

FIG. 5 is a diagrammatic representation of the interface of some of the components of the first embodiment;

FIG. 6 is a top view of the second embodiment in use;

FIG. 7 is an enlarged partial side view of the second embodiment of FIG. 6;

FIG. 8 is a partial enlarged side view of the injection device of the second embodiment;

FIG. 9 is a diagrammatic representation of the interface of some of the components of the second embodiment;

FIG. 10 is a front view of the third embodiment;

FIG. 11 is an enlarged partial view of the embodiment of FIG. 10;

FIG. 12 is a sectional view of the embodiment of FIG. 11 taken along lines A-A;

FIG. 13 is a front view of the embodiment of FIG. 10 detailing the injection system;

FIG. 14 is a sectional view of the embodiment of FIG. 13;

FIG. 15 is a diagrammatic representation of the interface of some of the components of the third embodiment;

FIG. 16 is a front view of the fourth embodiment; and

Figure 17:
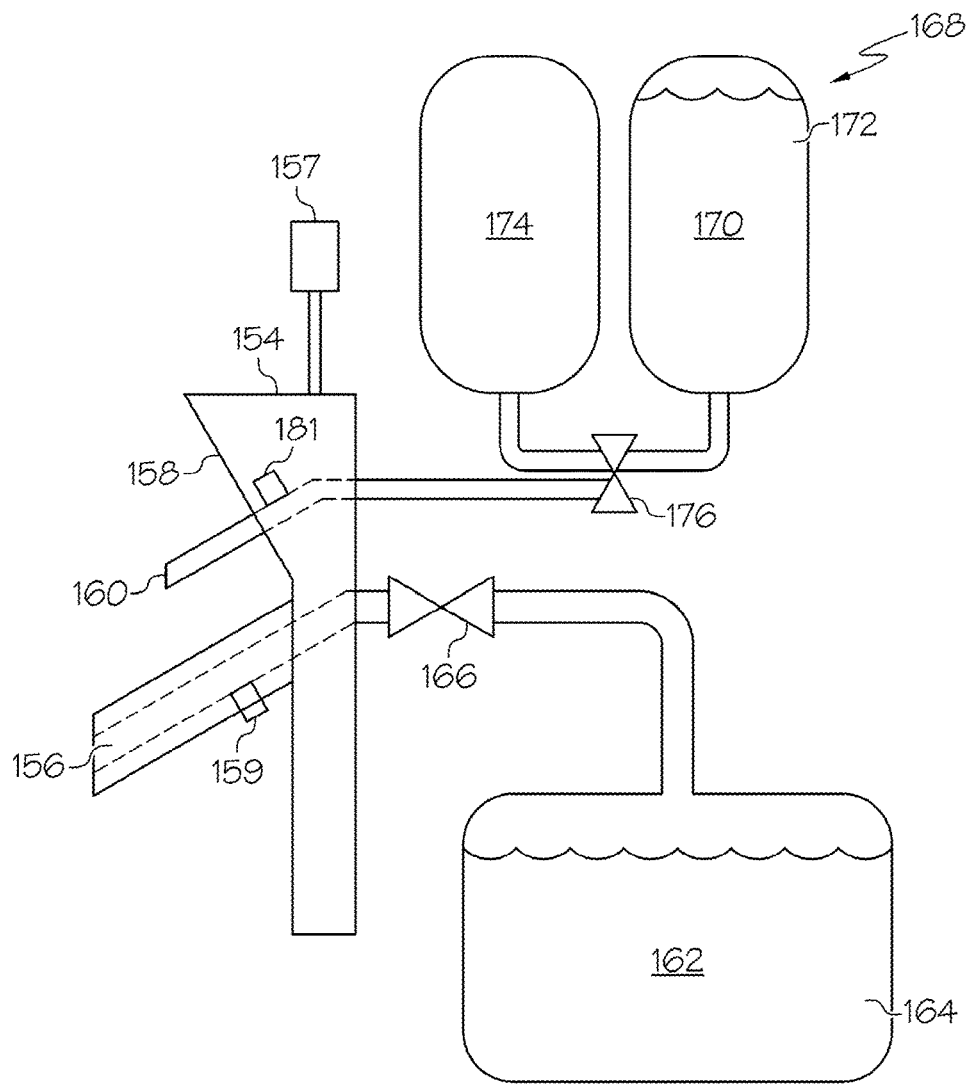

FIG. 17 is an enlarged detail view of a portion of the embodiment of FIG. 16.

Figure 18:
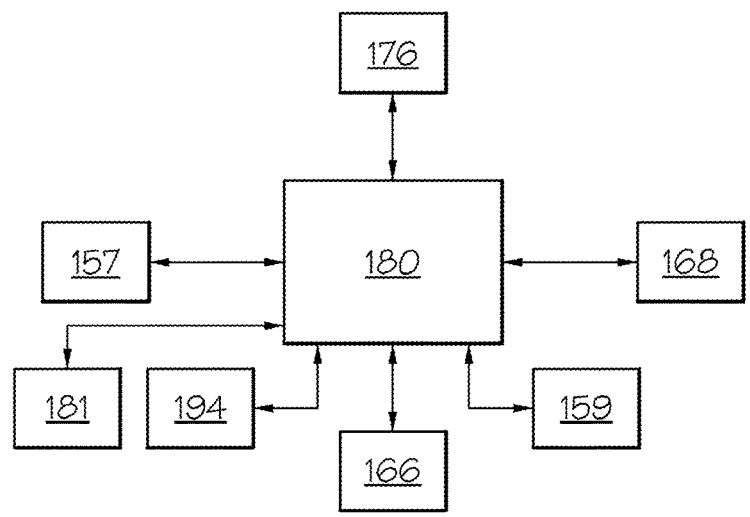

FIG. 18 is a diagrammatic representation of the interface of some of the components of the fourth embodiment;

DETAILED DESCRIPTION

The present disclosure is directed to automated systems and methods for effectively delivering a substance to an animal. Various aspects of the present disclosure will be described more fully hereinafter with reference to the accompanying drawings, in which some, but not all aspects of the disclosure are shown. Indeed, this disclosure may be embodied in many different forms and should not be construed as limited to the aspects set forth herein.

One embodiment is directed to the delivery of a substance to masses of chicken hatchlings after they have been separated from their shells and prior to departure from the hatchery. In addition, methods and systems according to aspects of the present disclosure relating to chicks may be used with any types of poultry including, but not limited to, chicken, turkey, duck, geese, quail, pheasant, and exotic birds, etc.

Another embodiment is directed to the delivery of a substance to cattle. However, the methods and systems according to various aspects of the present disclosures may be used with any type of livestock including but not limited to bison, pigs, goats, sheep, horses etc. A further embodiment is directed to the delivery of a substance to fish. It is anticipated that the methods and systems according to the various aspects of the present disclosures may be applied with any type of fish or shellfish including but not limited to farmed fish such cod, trout, salmon, tilapia, as well as shrimp, lobster, scallops, oysters, clams, mussels, crayfish, etc. Yet a further embodiment is directed to the substance delivery to swine. Like numbers refer to like elements throughout the multiple views.

FIG. 1 illustrates a top view of an overall system of the first embodiment 10. FIG. 2 illustrates a side view of the system in FIG. 1. The first embodiment 10 would likely be located in the day-of-hatch room in a chicken hatchery. The chick/shell separator 12 provides the means for separating the hatchling from its shell. A first conveyor 14 moves the chick—from the chick/shell separator 12 through an opening in the separating wall 16 to a second, wider conveyor 18. The separating wall 16 separates the hatchling process from the substance delivery process.

The second, wider conveyor 18 begins to spread the chicks out which makes processing each individual chick easier. From the second conveyor 18, the chicks are transported onto third, and forth conveyors 20, 22, which are wider than the second conveyor. As can be seen in FIG. 1, a fifth conveyor 24 has dividers 26 which may be suspended from the top of the conveyance assembly. The dividers 26 help to move the chicks into narrow rows which eventually become single file rows.

A sixth conveyor 28 includes dividers 26 to keep the chicks in the single file rows created on the fifth conveyor 24. The sixth conveyor 28 moves the single rows of chicks separated by the dividers 26 onto a series of similarly matching angled conveyor belts 30.

Individual carrier devices 32 are located below the angled conveyor belt 30. Each individual carrier device 32 is similar to a cup or basket and sized to receive a single chick 13, as shown in FIG. 3. The individual carrier devices 32 are interlinked and travel along an individual carrier pathway advanced by a conveyor system. Each carrier device 32 is hingedly mounted relative to the conveyor system so that each device can rotate or pivot about its hinged connection. The degree of rotation may be limited to ensure that the chick 13 does not fall out of the device 32.

The first embodiment 10 further includes an injection system 42 (FIG. 4). The injection system 42 has an injection head 44, substance reservoir 47 and pressurized gas supply 48, and an activation mechanism 50 as shown in FIG. 4. Pressurized gas may be delivered to the injection system 42 via pre pressurized gas capsules or alternatively via a gas plumbing attached to a centralized compressor.

The activation mechanism 50 is in communication with a system controller 38 (FIG. 4). The activation mechanism 50 activates the pressurized gas and substance to deliver a predetermined dosage amount to the chick 13. The substance reservoir 47 may contain a vaccine, medicament or biologic, for injection into the chick 13.

The injection system 42 and a camera 36 are mounted underneath the carrier device conveyor system 34 on an injection system moving platform 45 (FIG. 4). The injection system operates effectively for delivering an injection into the hind region of a chick 13. Thus, the injection system 42 is designed to inject only those chicks 13 that are sitting upright in the carrier device 32. The injection system moving platform 45 runs adjacent and parallel to the carrier device conveyor system 34 and at the same speed. This enables the camera 36 to capture an image of the chick 13 in the carrier device 32 while it is moving. This also enables the injection system 42 to operate while the chick 13 is travelling in the carrier device 32 which will be explained in further detail below.

A conveyor control system 40 controls the speed and operation of all the conveyor belts. The system controller 38 is in communication with the camera 36, the conveyor control system 40 and the injection system 42, as shown schematically in FIG. 5. The system controller 38 includes a computer processor and an image processor. The image processor receives images from the camera 36 and processes them. The system controller 38 is in communication with all sensors, cameras, conveyors, actuators and I/O (Input/Output receivers and drivers) of the overall system. The system controller synchronizes all system operations and acts the Brain of the System. The I/Os activates and deactivate the components and the system controller takes the info from the computer processor and image processor and activates the specific spray head.

Below the individual carrier devices 32 is a seventh conveyor belt 46 as shown in FIGS. 1 and 2. The seventh conveyor belt 46 moves the chicks 13 en mass into containers for transfer to a growing farm where they will be bred for consumption.

In use, a chick 13 once it has hatched, is separated from its shell in the chick/shell separator 12 (FIG. 1). The chick 13 then moves onto the first conveyor belt 14. As the chick 13 travels, the chick moves onto the second 18, third 20, fourth 22, fifth 24 and sixth 28 conveyor belts. Each conveyor belt spreads the chicks further apart until they are in single file formation on the sixth conveyor belt 28.

The chicks 13 move from the sixth conveyor belt 28 (FIG. 3) onto the angled conveyor belt 30 which drops them into the individual carrier devices 32. Below the individual carrier device 32, the camera 36 and injection system 42 travel parallel and at the same speed on the injection system moving platform 45. The camera 36 (FIG. 4) is positioned underneath the carrier device 32. The camera 36 captures at least one image of the chick 13 in the individual carrier device 32. The camera 36 relays the captured image to the system controller 38. The system controller 38 processes the image and determines the relative position of the chick 13 within the individual carrier device 32.

Having determined the relative position of the chick 13 within the carrier device 32, the system controller activates the injection system 42 below the carrier device where the chick is in a desired position for vaccination. If the system controller 38 determines the chick 13 is not in the desired position (e.g. the chick is not in the upright sitting position) the system controller 38 will not activate the injection system 42 (FIG. 5).

Once activated, the activation mechanism 50 of injection system 42 (FIG. 4) causes an amount from the pressurized gas supply 48 to move a predetermined volume of substance from the reservoir 47 to move through the injection head 44 and into the chick 13. Preferably, at the time of delivery the injection head 44 is adjacent to or in contact with the chick 13.

After injection, the carrier device 32 travels to the end of the carrier device conveyor system 34 (FIG. 3). As the conveyor system rotates the hingedly connected carrier devices 32 also rotate. This causes the chick 13 held therein to fall gently onto the extended hinged slide 33 and onto the seventh conveyor belt 46 if the chick 13 was vaccinated. For chicks that did not receive an injection because they were not in appropriate position in the carrier device 32, the hinged slide 33 will pull back to a perpendicular position and the chick will fall gently on conveyor 47 and travel back by other conveyance not shown and be placed on conveyor 24 to go through the process once again and obtain an injection.

After the injection, the camera 36 and injection system 42 (FIG. 4) on the injection system moving platform 45 are pulled back to their initial position and begin to travel below the individual carrier devices 32 again. The mechanism that controls the function of the moving platform is controlled by the system controller 38.

It should be appreciated that while the discussion above relating to injection devices focused on needle-free devices, it is anticipated that a needle injection device may also be used. Vaccines envisioned to be delivered by way of injection include but are not limited to Marek's and herpes virus of turkey (HVT) vectored vaccines.

A second embodiment 70 is shown in FIG. 6. The second embodiment 70 includes a pen 72 and a series of dividers 74 for encouraging livestock, such as young cattle 75, to move therethrough. The dividers 74 are arranged in a parallel fashion and have forward and aft gates 77, 79 respectively. The forward gate 77, when closed, prevents the animal from traveling forward beyond the forward gate and out of the dividers 74 and pen 72. The aft gate 79, when closed, prevents the animal from backing up out of the dividers 74 and back into the pen 72.

A presence sensor 76, shown in FIGS. 6 and 7, is mounted onto or near the divider 74 and positioned to sense a calf 75 moving between a pair of dividers. A presence sensor 73, shown in FIGS. 6 and 7, is mounted onto or near the divider 74 and positioned to sense a calf 75 reaching the proximity of the forward gate 77 (FIG. 7). An electronic reader 93 is mounted onto or near divider 74 to read the electronic identification tags 88 of the livestock. Camera 78 is mounted above the divider 74 so that the camera is able to obtain a full image of the calf 75 and that the camera would not be struck by the calf. Camera 78 captures at least one image of the calf, which may include a predetermined target area on the calf 75, such as the upper portion of the right hind leg.

The second embodiment 70 further includes an automated injection system 82 (FIG. 8). The injection system has a reservoir 84 filled with a substance 86, such as a vaccine, drug, biologic or other medicament used to treat the subject animal, in this case, a calf 75. The injection system 82 also includes a pressurized gas supply 90 and an injection head 91. Pressurized gas may be delivered to the automatic injection system 82 via pre pressurized gas capsules or alternatively via a gas plumbing attached to a centralized compressor.

The injection system 82, shown in FIG. 8, is adjustably mounted to a frame 92 that allows for automatic adjustment to the height, depth and length of the injection system. The frame 92 is fixedly mounted to a fixed structure such as one or more of the dividers 74. The automatic adjustability of the injection system 82 is achieved by mechanisms (not shown) that can automatically and remotely adjust the height, width and depth of the injection system 82 relative to the position of the calf 75. Details of the adjustability will be explained in further detail below.

The pressurized gas supply 90 (FIG. 8) may be used to deliver the substance 86 within the reservoir 84 into the calf 75. It is appreciated that the control of the pressurized gas supply 90 and substance 86 are understood by those skilled in the art of needle-free delivery devices.

A system controller 80 is in electronic communication with the presence sensor 76, camera 78 and injection system 82, as shown schematically in FIG. 9. The system controller 80 communicates with the presence sensor 76, presence sensor 73, forward gate 77, aft gate 79, electronic reader 93 (FIG. 7), camera 78 and injection system 82 to deliver a predetermined dosage of a substance 86 to a predetermined target area on the calf 75. The system controller 80 includes a computer processor and an image processor. The system controller 80 has the capability to remotely control the operation of the presence sensor 73, gates 77, 79, electronic reader 93, camera 78 and injection system 82. Moreover, the system controller 80 processes the images received from the camera 78. The details of this methodology are discussed in more detail below.

In use, as shown in FIG. 6, a pen 72 holds a group of livestock, but the dividers 74 encourage a single calf 75 to move forward between a pair of dividers. As the calf 75 moves between the dividers 74, the presence sensor 76 activates and communicates with the system controller to close the forward gate 77 to prevent any further forward travel by the calf. Subsequently, as the calf 75 reaches the presence sensor 73, the system controller 80 also closes the aft gate 79 to stop any rearward travel by the calf 75 and prevent the calf from backing out of the dividers 74. At this point the calf 75 is held relatively stationary between a pair of dividers 74 and the forward and aft gates 77, 79 respectively.

In addition, the presence sensor 73 (FIG. 6) communicates with the camera 78 to begin capturing video footage of the calf 75 and in particular, the relative position of the predetermined area on the calf. For example, if the substance is preferably delivered to the upper right hind leg ("target area") then the camera 78 can be preprogrammed to focus in on the target area. Once the image camera 78 captures the images of the calf's target area, the images are relayed to the system controller 80.

The system controller 80 (FIG. 9) analyzes the images and communicates with the automatic injection system 82 mounted on the adjustable frame 92. The system controller 80 signals the automatic injection system 82 to make any necessary positional adjustments to the height, angle or length of itself and depth of the injection head 91 relative to the target area. A predetermined amount of substance is drawn from the reservoir 84 and injected into the target area of the calf 75 through the injection head 91 (FIG. 8) using pressurized gas from the gas supply 90.

After the injection is given, the system controller opens the forward gate 77 (FIG. 6) which enables the calf 75 to move out from the dividers 74 and into another part of the facility. The aft gate 79 is subsequently opened which allows another calf 75 to move between the dividers 74 and the process repeats itself.

It should be noted that an electronic reader 93 (FIG. 7) is positioned to digitally read an identification tag 88 typically fixed to a calf's ear. In this case, the electronic reader 93 may also scan the data available on the tag 88 to specifically identify that particular calf 75. Furthermore, once the vaccination has occurred, the system controller 80 would record the type of vaccination and date of delivery into its database which would be accessible via the calf's tag 94. In addition, should the calf 75 finds its way back into the pen 72, the system controller 80 after receiving identity information from the electronic reader 92, recognizing that the calf 75 was already vaccinated, opens the forward gate 77, enabling the calf 75 to move out and preventing a re-vaccination of the calf 75.

It is anticipated that the injection system of the second embodiment 70 is applicable to other livestock such as pigs, sheep, goats, bison and the like. It is appreciated that the size and spacing of the dividers 74 as well as the range of adjustability in the frame 90 would likely be altered for each different aforementioned animal.

Vaccines or substances that may be delivered to livestock, mainly cattle, include but are not limited to Blackleg, malignant edema, enterotoxemia C & D, IBR, PI3, clostridial, BRSV, *Pasteurella*, MLV-IBR/PI3, K-BVD, MLV-BRSV, Brucellosis, and/or Lepto.

Vaccines or substances that may be delivered to livestock, mainly sheep, include but are not limited to *campylobacter, vibrio, chlamydia, clostridium* perfringes C & D, tetanus, intranasal parainfluenza, clostridial, Orf, and/or Foot rot.

A third embodiment 100 is provided in FIG. 10. The third embodiment 100 is directed to the delivery of a substance to a fish 104. The third embodiment 100 includes a first tank 106 and a second tank 108. The first 106 and second tanks 108 are connected by means of a pipe 110. The size and length of the pipe 110 will depend on the type of fish 104 held in the tanks, 106, 108.

Forward and rearward bladders 112, 114 (FIG. 11) respectively are located at either end of the pipe 110 so as to prevent fish 104 travel along the pipe into the first 106 and second 108 tanks, as shown in FIG. 11. Each bladder 112, 114 is in communication with a pressurized fluid source 116 (FIG. 10) and activated remotely. In addition, each bladder 112, 114 (FIG. 11) can be quickly inflated and deflated.

Right and left side bladders 118, 120 respectively are located on the corresponding right and left sides of the pipe 110, as shown in FIG. 12. As with the forward and rearward bladders discussed above, the right 118 and left 120 side bladders are also in communication with the pressurized fluid source 116 and activated remotely. The right and left side bladders 118, 120 are also quickly inflated and deflated.

Returning to FIG. 10, first tank bladder 122 is located at the bottom of the first tank 106. Similarly, a second tank bladder 124 is located at the bottom of the second tank 108. Both bladders, 122, 124 are in communication with the pressurized fluid system 116. The pressurized fluid system 116 controls the flow of fluid into and out of each bladder 122, 124 which will be discussed in detail below. The tank bladders 122, 124 are large enough to achieve a similar volume to the first 106 and second tanks 108.

A presence sensor 126, shown in FIG. 11, is mounted on the pipe 110 and located near the rearward bladder 114. The presence sensor 126 is designed to sense the presence of a fish 104 within the pipe 110. A camera 128 is also mounted on the pipe 110 between the forward and rearward bladders 112, 114. The camera 128 is preferably a video camera capable of capturing live video images of the fish 104 within the pipe 110. In particular, the camera 128 is designed to take video footage of a predetermined target area on the fish 104. For example, it is desirable to deliver injections into an Atlantic Salmon below the pleural ribs and aft of the pelvic fin. Conversely with Tilapia, injections are often made behind either of the side fins. Because the target area will vary for different types of fish, the camera 128 would need to be preprogrammed to focus on a particular predetermined target area of the subject fish to be treated.

FIG. 13 shows an injection system 130 having a reservoir 132 of substance 134 for injection, a pressurized gas source 138 (FIG. 13) and injector head 140 (FIG. 14). The injection system 130 is mounted on the interior of the pipe 110 between the forward and rearward bladders 112, 114. The injection system 130 may be mounted on the bottom, as shown in FIG. 11, or side, as shown in FIG. 14, of the pipe 110 depending on the type of fish to be treated.

The injector head 140 (FIG. 14) is movably mounted to a frame (not shown) within the injection system 130. It is appreciated that the injector head 140 has the ability to move axially and radially along the interior wall of the pipe 110. The movement of the injector head 140 would be controlled remotely by a system controller 146 (FIG. 15).

The presence sensor 126, camera 128, injection system 130 and pressurized fluid source 116 are all in communication with a system controller 146 (FIG. 15). The system controller 146 includes a computer processor and an image processor. The system controller is capable of remotely controlling the presence sensor 126, camera 128, injection system 130 and pressurized fluid source 116. The system controller 146 receives the positional information provided by the camera 128 and processes it to automatically adjust the position of injector head 140 and the timing of the injection as will be explained in more detail below. The system controller communicates with the pressurized fluid source 116 to deflate and inflate the forward 112, rearward 114, right side 118, left side 120, first 122 and second tank 124 bladders.

In use, the fish 104 are all located in the first tank 106. For this example, we assume all of the fish 104 are salmon. The first tank 106 has a relatively high volume of water and a high number of fish 104, as shown in FIG. 10. The first tank 106 is connected to the second tank 108 by means of the pipe 110. The second tank 108 has a low volume of water and a preferably no fish. The forward and rearward bladders 112, 114 are in an inflated position so that fish 104 are blocked from entering the pipe 110.

To deliver the substance to the fish 104, the rearward bladder 114 is deflated. This enables a fish 104 to swim into the pipe 110 and towards the second tank 108. However, the presence sensor 126 senses the presence of a fish 104 in the pipe and signals that system controller 146. The system controller causes the forward bladder 112 to inflate so as to block further forward movement of the fish 104 towards the second tank 108. Also, as the fish 104 passes beyond the presence sensor 126, the system controller 146 is signaled to inflate the aft bladder 114, securing that no other fish 104 enters the pipe 110.

The presence sensor 126 also signals to the camera 128 to activate (FIG. 11). The camera 128 captures video images of the predetermined target of the fish 104. This may vary between species of fish. For salmon, the preferred delivery area is the bottom of the fish between the pleural ribs and aft of the pelvic fin.

Once the camera 128 captures an image of a predetermined area of the fish 104, the image is sent to the system controller 146 for processing (FIG. 15). Based on the fish's position, as captured by the camera 128, the system controller 146 will remotely adjust, if necessary, the position of the injector head 140 relative to the fish 104 to place the injector head within the target area. In particular, the system controller 146 will control the height, width and depth of the injector head 140 relative to position of the fish 104, as determined by the camera 128, and will control the activation of the injection. Thus once the fish 104 has moved into a predetermined position along the pipe 110, the injection head position will adjust accordingly and under the control of the system controller 146.

It is also anticipated that rather than controlling the position of the injector head 140, the system controller may control the position of the fish 104 (FIG. 12). By manipulating the pressure of the forward 112, rearward 114, right side 118 and left side 120 bladders, the system controller may be able to alter the position of the fish 104 so that the target area is directly adjacent to the injector head 140.

Once the injection has been delivered to the fish 104, the system controller 146 communicates with the forward bladder 112 and side bladders 118, 120 to rapidly deflate them (FIGS. 12 & 15). The deflation of the side bladders 118, 120 no longer restrains the fish 104. The deflation of the forward bladder 112 allows the fish 104 to move forward and into the second tank 108. The rearward bladder 114 is then deflated which allows another fish 104 to move into the pipe 110 and the process repeats itself.

It should be noted that as each fish 104 swims into the second tank 108, the first tank bladder 122 and the second tank bladder 124 adjust in volume of water accordingly (FIG. 10). For example, as the first tank 106 begins to empty its population of fish 104 into the second tank 108, the first tank bladder 122 begins to slowly inflate. As it does, the volume of water in the first tank 106 declines. Conversely, as the second tank 108 begins to fill with fish 104 from the first tank 106, the volume of water in the second tank needs to increase. The second tank bladder 124 slowly deflates and thus allows the volume of water in the tank to increase to accommodate the greater population of fish 104. The rates at which the first 122 and second tank bladders 124 inflate and deflate are controlled by the system controller 146. It is appreciated that the system controller 146 is in communication with the pressurized fluid source 116 to remotely open and close the appropriate valves to each component mentioned herein to accomplish this task.

It is further appreciated that a false bottom may rest atop each tank bladder to provide a more even surface for the tank. This may be important in ensuring that the first tank is completely emptied of fish prior to refilling with a new tank.

With respect to fish, vaccines or other substances that may be delivered include but are not limited to furunculosis vaccine for salmon, koi herpes virus in koi, vaccines or drugs may be delivered to treat VHS, ich and whirling disease in some commercially important fish.

A fourth embodiment 150 is shown in FIG. 16. The fourth embodiment 150 is focused on the intra nasal delivery of specific vaccines and other medicament to piglets 152.

The fourth embodiment 150 includes a contoured element 154, shown in detail FIG. 16 and in detail in FIG. 17. Each contoured element 154 has a nipple 156 extending therefrom. The contoured element 154 is shaped to receive the face of a piglet 152 and includes a contoured space to receive a piglet's snout. In addition, the contoured element 154 has a snout receiving plate 158 upon which the end of a piglet's 152 snout is designed to rest. The snout receiving plate 158 has a pair of hollow fingers 160 protruding outwardly from the contoured element 154. The pair of fingers 160 are sized and spaced to be received into the nostrils of a piglet 152 when the piglet takes the nipple 156 into its mouth, which will be explained in detail below.

The plurality of contoured elements 154 are fixedly mounted to a surface, such as a vertical wall (FIG. 16). Each nipple 156 is equipped with a pressure sensor 159 which is in communication with a system controller 180 as shown in FIG. 18. Each nipple 156 is also connected to a tank 162 of liquid formula. A valve 166 operable by the system controller 180 opens and closes the flow of formula from the tank 162 to the nipple 156.

The pair of hollow fingers 160 are equipped with a sensor 181 which will be activated once both fingers 160 are received into the piglet's nostrils (FIG. 17). The sensor 181 is in communication with the system controller 180 and connected to a pressurized substance delivery system 168, shown in detail in FIG. 17. The pressurized substance delivery system 168 includes a container 170 housing a supply of substance 172, such as a vaccine. The pressurized substance delivery system 168 also includes a pressurized gas source 174 in communication with the container 170 of substance 172, as well as a control mechanism 176 that activates and terminates delivery of the substance under pressure and is also controlled by the system controller 180.

Thus, the pressurized substance delivery system 168, and the valve 166 controlling flow of the formula 164 through the nipple 156, are in electronic communication with each other via the system controller 180. The advantages and logistics of such communication will be explained in more detail below when discussing the operation of the fourth embodiment 150.

The floor on which the piglet stands to suckle is a platform 190 having a hinge 192 and a latch 194. The latch 194 is remotely controlled by the system controller 180. The platform 190, hinge 192 and latch 194 act like a trap door to prevent suckling by a pig that has already received a substance. The function of the platform 190 will be explained in further detail below.

In use, piglets 152 are brought to a holding area where a plurality of contoured elements 154 are fixedly mounted. This may occur through a series of conveyor belts and dividers or it may be accomplished manually. For the most effective results, it is desirable that the piglets 152 be hungry and/or thirsty. The nipple 156 is presented to the piglet 152 and the piglet will instinctively latch onto to it and begin to suck. As the piglet 152 latches onto the nipple 156 and start suckling, the pressure sensor 159 is activated and informs the system controller 180 of the presence of the piglet 152. Meanwhile, the piglet's snout will be received into the snout receiving plate 158 of the contoured element 154. In addition, the pair of fingers 160 will be received into the piglet's nostrils and sensed by sensor 181. Sensor 181 communicates the engagement of piglet's nostrils to the system controller 180.

As the piglet 152 suckles the nipple 156, the valve 166 regulating the flow of formula 164 (FIG. 16) is activated by the system controller 180 (FIG. 18) to open and a dosage of formula will flow from the tank 162 through the nipple 156 and into the piglet's mouth. Concurrently, the pressurized substance delivery system 168 is also activated. The substance 172, such as a vaccine, is delivered under pressurized fluid through the nasal passage of the piglet 152. The pressure of the delivery is designed to deliver the dosage through the nasal passage or intra cartilage but not cause damage.

After the pressurized substance delivery system 168 (FIG. 18) has delivered its dosage, a signal is sent from the pressurized substance delivery system 168 to the system controller 180. The system controller 180 triggers the valve 166 to close. The valve 166 closing causes the flow of formula 164 to the nipple 156 to cease and the piglet 152 is encouraged to move away from the nipple 156. This may be accomplished by retracting the nipple 156 behind the contoured element 154. This may also be accomplished by causing an obstruction between the piglet 152 and the nipple 156, such as a robotic lowering of floor under the piglet 152. Once the piglet 152 is no longer able to suckle the nipple 156, the piglet will be moved on for further processing.

It should be noted that an electronic reader 157 (FIG. 16) is positioned to digitally read an identification tag 182 typically fixed to the piglet's ear. In this case, the electronic reader 157 may also scan the data available on the tag 182 to specifically identify that particular piglet 152. Furthermore, once the vaccination has occurred, the system controller 180 would record the type of vaccination and date of delivery into its database which would be accessible via the piglet's tag 182.

Should the piglet 152 finds its way back to the fourth embodiment 150, the system controller 180 after receiving identity information from the electronic reader 157, recognizing that the piglet 152 was already vaccinated, prevents re-vaccination of the piglet 152 (FIGS. 16, 17, 18). The system controller 180 does not activate the flow of formula from the nipple 156 or the substance delivery system 168. In addition, system controller 180 communicates with the latch 194 to open it. This results in the platform 190 rotating about the hinge 192 and allowing the piglet to fall to a level below for further processing. It is envisioned that any number of devices may be employed to prevent the piglet from being treated more than once. The system described above is provided by way of example and not limitation.

It should be appreciated that certain vaccines and/or medicaments are preferably delivered through the nasal cavity or soft cartilage of a piglet 152. These include but are not limited to *Mycoplasma, Haemophilus Parasuis*, Pleuropneumoniae, *Actinobacillus*, PRRS, Swine flu, and swine PEDV.

It should be appreciated that while the discussion above focused on vaccines and medicaments, a person of skill in the art would know that the substance delivered could include any number of substances used to vaccinate, medicate or otherwise treat livestock, mammals, including humans, or any number of other animals.

It is expected that many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not intended to be limited to the specific aspects disclosed and that modifications and other aspects are intended to be included within the scope of the appended claims. Although specific terms are employed herein, they are used in a generic and descriptive sense only and not for purposes of limitation.

The invention claimed is:

1. A system for automatically delivering a substance to a predetermined area of a fish comprising:
   a first tank having a first volume of water, the first tank sized to hold at least one fish;
   a second tank having a second volume of water, the second tank sized to receive at least one fish;
   a pipe in fluid communication between the first and second tanks, the pipe having a first end proximate to the first tank and a second end proximate to the second tank;
   a positioning device that positions a fish having a predetermined delivery area, the positioning device located in the pipe and comprising a pair of opposing inflatable bladders, the bladders in fluid communication with a pressurized fluid source;
   forward and rearward bladders, each bladder in fluid communication with the pressurized fluid source;
   an image capture device to capture at least one image of a relative position of the fish; a delivery system to deliver a predetermined dosage of a substance to the predetermined delivery area of the fish;
and
   a system controller in communication with the positioning device, image capture device and delivery system.

2. The system of claim 1 wherein the pressurized fluid source is activated remotely.

3. The system of claim 1 wherein the substance is a vaccine, medicament or biologic.

4. The system of claim 1 wherein the substance may be used to treat one or more of the following: furunculosis, koi herpes virus, Viral Haemorrhagic Septicaemia, ich and whirling disease.

5. The system of claim 1 wherein the image capture device is a camera.

6. The system of claim 1 wherein the system controller includes a computer processor.

7. The system of claim 1 wherein the fish is positioned individually.

8. The system of claim 1 wherein the delivery system is an injector.

9. The system of claim 8 wherein the injector is needless.

10. A system for automatically delivering a substance to a predetermined area on a fish comprising:
    a first tank having a first volume of water, the first tank containing at least one fish, the fish having a predetermined delivery area;
    a second tank having a second volume of water, the second tank to receive the at least one fish from the first tank;
    a pipe in fluid communication between the first and second tanks and into which a fish may travel from the first tank to the second tank;
    a pair of opposing inflatable bladders, the bladders in fluid communication with a pressurized fluid source, the pair of opposing bladders, when inflated, restrain the fish individually; forward and rearward inflatable bladders located on either side of the pair of opposing bladders, the forward and rearward bladders each in fluid communication with a pressurized fluid source, the forward and rearward bladders when inflated block the fish a forward and rearward movement of the fish in the pipe;
    an image capture device to capture at least one image of a relative position of the predetermined delivery area on the fish;
    a positionally adjustable delivery system to deliver a predetermined dosage of a substance to the predetermined delivery area on the fish; and
    a system controller in communication with the pair of opposing bladders, forward and rearward bladders, image capture device and delivery system.

11. The system of claim 10 further comprising a presence sensor to sense the presence of a fish in the pipe.

12. The system of claim 10 wherein the delivery device is an injector.

13. The system of claim 12 wherein the injector is needle-free.

14. The system of claim 10 wherein the substance may be used to treat one or more of the following: furunculosis, koi herpes virus, Viral Haemorrhagic Septicaemia, ich and whirling disease.

15. The system of claim 10 wherein the pair of opposing bladders is located in the pipe.

16. The system of claim 10 wherein the image capture device is a camera.

17. The system of claim 10 further comprising a first tank bladder located in the first tank and a second tank bladder located in the second tank, the first and second tank bladders in fluid communication with a pressurized fluid source.

18. The system of claim 17 wherein the system controller is capable of controlling the first volume of water in the first tank by controlling a flow of fluid from the pressurized fluid source to the first tank bladder, and controlling the second volume of water in the second tank by controlling a flow of fluid from the pressurized fluid source to the second tank bladder.

* * * * *